United States Patent [19]

Portnoy

[11] Patent Number: 4,497,807
[45] Date of Patent: Feb. 5, 1985

[54] THIADIAZINONE PLANT DISEASE CONTROL AGENTS

[75] Inventor: Robert C. Portnoy, Wilmington, Del.

[73] Assignee: E. I. Du Pont de Nemours and Company, Wilmington, Del.

[21] Appl. No.: 892,405

[22] Filed: Mar. 31, 1978

[51] Int. Cl.³ ............................................. A01N 43/88
[52] U.S. Cl. ........................................ 514/222; 544/8
[58] Field of Search ............................ 544/8; 424/246

[56] References Cited

U.S. PATENT DOCUMENTS 4,097,594  6/1978  Peake et al. ............................... 544/8
4,100,281  7/1978  Peake et al. ............................... 544/8

FOREIGN PATENT DOCUMENTS 854184  11/1977  Belgium .

OTHER PUBLICATIONS

Geevers et al., Rec. Trav. Chim., vol. 93, pp. 270–272 (1974).

Primary Examiner—Allen J. Robinson

[57] ABSTRACT

Thiadiazinones, such as 3-chloro-5-phenylthio-4H-1,2,6-thiadiazin-4-one, useful for control of certain fungus plant diseases such as scab of apple, late blight of tomato and downy mildew of grape.

12 Claims, No Drawings

THIADIAZINONE PLANT DISEASE CONTROL AGENTS

BACKGROUND OF THE INVENTION

This invention relates to thiadiazinone antifungal agents for plants.

In *Rec. Trav. Chim. Pays Bas,* 93, 270 (1974) is reported the synthesis of various thiadiazinones including

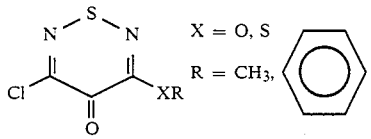

No utility is disclosed for these compounds.

SUMMARY OF THE INVENTION

This invention relates to compounds of Formula I, to agriculturally useful compositions of these compounds, and to their method of use as plant disease control agents.

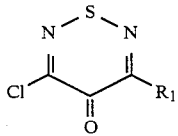 (I)

wherein
$R_1 = SR_2$ or $OR_3$;
$R_2$ = alkyl of 1 to 6 carbon atoms,

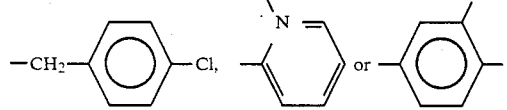

$X = H$ or $Cl$,
$Y = H$, $Cl$ or alkyl of 1 to 4 carbon atoms,
$R_3$ = alkyl of 1 to 6 carbon atoms or

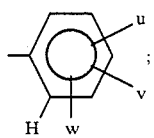

$u = H$, F, Cl, Br, I, alkyl of 1 to 4 carbon atoms, alkoxy of 1 to 3 carbon atoms, $NO_2$, CN, $CO_2CH_3$, $CO_2C_2H_5$ or $N(CH_3)_2$;
$v = H$, Cl, methyl or methoxy;
$w = H$ or Cl;
provided that when $X = Cl$, then $Y = Cl$.

Compounds within the scope of Formula I wherein
$R_2 = CH_3$ or

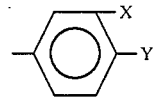

where X and Y both are H and
$R_3 = CH_3$ or

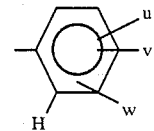

where u, v and w are all H are known in the prior art, but their use for control of plant diseases has not been previously disclosed.

DETAILED DESCRIPTION OF THE INVENTION

Preferred Compounds

Preferred for high activity, and/or ease of synthesis, and/or favorable cost are those compounds of Formula I wherein
$R_2$ = methyl,

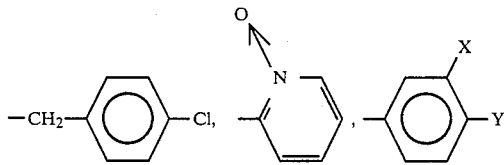

where $X = H$;
$R_3$ = methyl or

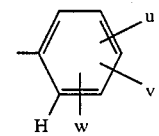

wherein;
$u = H$, Cl, methyl or methoxy;
$v = H$, Cl, methyl or methoxy;
$w = H$ or Cl.

More preferred for their higher activity, and/or ease of synthesis, and/or more favorable cost are compounds of Formula I wherein
$R_2$ = methyl,

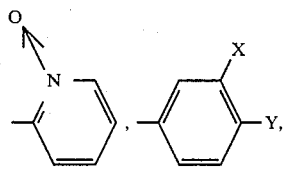

wherein $X = H$ and $Y = H$, Cl or $C(CH_3)_3$;
$R_3 =$

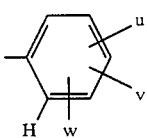

wherein
u=H, Cl, methyl or methoxy;
v=H or Cl;
w=H or Cl.
Specifically preferred are those compounds where
R₂=methyl,

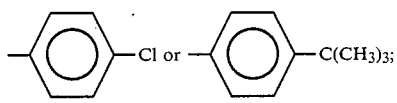

R₃=

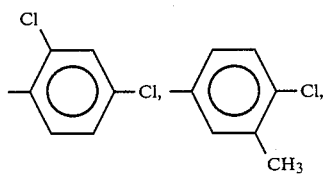

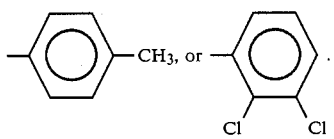

Synthesis

Starting material for synthesizing the thiadiazinone plant disease control agents of this invention is 3,5-dichloro-4H-1,2,6-thidiazin-4-one prepared according to the method disclosed in *Rec. Trav. Chem. Pays Bas,* 93, 270 (1974).

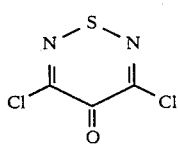

3,5-Dichloro-4H—1,2,6-thiadiazin-4-one.

The thiadiazinones of this invention are all obtained by the procedures disclosed in the same reference. In general the process comprises mixing starting material with an appropriate solvent and treating it with a molecular equivalent quantity of an alcohol, alkanethiol, phenol, thiophenol or benzylthiol in the presence of a base such as an alkali metal hydroxide or alkoxide, alkali metal carbonate, metal hydride, or a tertiary amine.

Various specific reaction conditions utilized to prepare the compounds of this invention are fully described in the following examples. All parts are by weight and temperatures are in degrees Centigrade unless otherwise specified.

EXAMPLE 1

3-chloro-5-phenylthio-4H-1,2,6-thiadiazin-4-one

A mixture of 3.66 g of 3,5-dichloro-4H-1,2,6-thiadiazin-4-one, 30 ml of ethyl ether, and 2.02 g of triethylamine is stirred at 0°–5° C. while a solution of 2.20 g of thiophenol in 20 ml of ethyl ether is added dropwise to it. This mixture is stirred 2 hours longer while it is allowed to return to ambient temperature. Then it is filtered to remove triethylamine hydrochloride, and the filtrate is concentrated on a rotary evaporator. The solid residue is recrystallized from hexane to yield yellow prisms, mp 100°–2°.

The materials described in Table I are prepared by the same procedure as Example 1 by substituting the appropriately substituted thiophenol or benzenethiol for thiophenol. In this Table, for Formula I compounds, R₂=

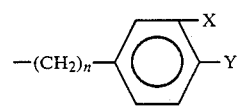

where n, X and Y are as defined.

TABLE I

| n | X | Y | mp °C. |
|---|---|---|--------|
| 0 | H | Cl | 132–4 |
| 0 | H | CH₃ | 106–8 |
| 0 | H | C(CH₃)₃ | 132–4 |
| 0 | Cl | Cl | 112–4 |
| 1 | H | Cl | 110–3 |

EXAMPLE 2

3-chloro-5-(4-chlorophenoxy)-4H-1,2,6-thiadiazin-4-one

A suspension of 1.83 g of 3,5-dichloro-4H-1,2,6-thiadiazin-4-one in 100 ml of water is stirred mechanically at room temperature while a solution of 1.29 g of p-chlorophenol, 20 ml of H₂O and 5 ml of 2N aqueous sodium hydroxide solution is added dropwise to it. The mixture is stirred an additional 1 hour. The resulting precipitate is collected and recrystallized from alcohol. The white crystals melt at 142°–145°. The compounds described in Table II can be prepared by the same procedure as Example 2 substituting the appropriate phenol for p-chlorophenol.

In this Table for Formula I compounds, R₃=

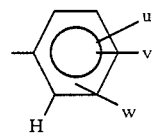

where u, v and w are as defined.

TABLE II

| u | v | w | mp °C. |
|---|---|---|--------|
| 4-OCH₃ | H | H | 142–5 |
| 4-CH₃ | H | H | 132–4 |
| 2-Cl | 5-Cl | H | 135–7 |
| 2-NO₂ | H | H | 137–9 |
| 3-CH₃ | H | H | 101–102 |
| 3-CH₃ | 4-Cl | H | 158–160 |
| 3-Cl | H | H | 98–100 |

TABLE II-continued

| u | v | w | mp °C. |
|---|---|---|---|
| 2-Cl | 4-Cl | H | 114–116 |
| 2-Cl | 3-Cl | H | 134–6 |
| 4-CH(CH$_3$)$_2$ | H | H | 114–116 |
| 2-I | H | H | 110–112 |
| 3-Cl | 5-Cl | H | 131–3 |
| 3-Cl | 4-Cl | 5-Cl | 157–9 |
| 2-Cl | 3-Cl | 5-Cl | 126–8 |
| 2-Cl | 4-Cl | 5-Cl | 163–5 |
| 4-Br | H | H | 145–7 |
| 4-F | H | H | 136–8 |
| 4-OCH$_2$CH$_2$CH$_3$ | H | H | |
| 4-C(CH$_3$)$_3$ | H | H | 161–163 |
| 2-CO$_2$CH$_3$ | H | H | |
| 2-CO$_2$C$_2$H$_5$ | H | H | |
| 2-CN | H | H | |
| 2-CH$_3$ | 5-CH$_3$ | H | |
| 3-N(CH$_3$)$_2$ | H | H | 130–132 |

EXAMPLE 3

3-chloro-(3,5-dimethoxyphenyl)-4H-1,2,6-thiadiazin-4-one

To a solution of 1.83 g of 3,5-dichloro-4H-1,2,6-thiadiazin-4-one in 50 ml CH$_2$Cl$_2$ is added a solution of 50 ml of water, 1.54 g of 3,5-dimethoxyphenol, 5 ml of 2N aqueous sodium hydroxide solution and 0.1 g of tetra-n-butylammonium chloride. The two phase mixture is stirred at room temperature for 3 hours. Then the layers are separated, and the organic layer is dried over magnesium sulfate and concentrated. The residue is recrystallized from alcohol to yield white crystals, mp 121°–124°.

EXAMPLE 4

3-chloro-5-methoxy-4H-1,2,6-thiadiazin-4-one

A solution of 3.66 g of 3,5-dichloro-4H-1,2,6-thiadiazin-4-one in 30 ml of methanol is kept at 0°–5° C. and stirred while a solution of 2.40 g of sodium methoxide in 30 ml of methanol is added dropwise to it. The reaction mixture is stirred at room temperature 2 hours longer, then mixed with 200 ml of ice water. The precipitate is collected, washed with water, dried, and recrystallized from hexane to yield pale yellow needles, mp 159°–161°.

EXAMPLE 5

3-chloro-5-propylthio-4H-1,2,6-thiadiazin-4-one

A well stirred solution of 1.83 g of 3,5-dichloro-4H-1,2,6-thiadiazin-4-one, 1.01 g of triethylamine and 30 ml of ethyl ether is kept at 0°–5° while a solution of 0.76 g of 1-propanethiol in 40 ml of ethyl ether is added dropwise to it. The reaction is then stirred 2 hours longer at room temperature and then filtered to remove triethylamine hydrochloride. The filtrate is concentrated and the residue purified by dry column chromatography on silica gel using benzene as eluent. The resulting product is a pure yellow oil.

The materials described in Table III can be prepared by the same procedure as Example 5 by substituting the appropriate alkylthiol for 1-propanethiol.

TABLE III

| R$_2$ | Physical Form |
|---|---|
| —CH(CH$_3$)$_2$ | yellow oil |
| —C(CH$_3$)$_3$ | orange oil |
| —CH$_3$ | |
| —(CH$_2$)$_5$CH$_3$ | |

EXAMPLE 6

3-chloro-5-(1-oxopyridin-2-ylthio)-4H-1,2,6-thiadiazin-4-one

A mixture of 1.83 g of 3,5-dichloro-4H-1,2,6-thiadiazin-4-one, 30 ml of tetrahydrofuran, and 1.49 g of 1-oxopyridine-2-thiol sodium salt is stirred at room temperature for 24 hours. Then the mixture is filtered to remove sodium chloride and other insolubles and the filtrate is concentrated to a solid residue which is recrystallized from ethanol. The product is yellow needles, melting at 129° with vigorous decomposition.

Formulation

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 1% to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Co., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 4th. Edn., McGraw-Hill, N.Y., 1963, pp. 8–59ff.

For further information regarding the art of formulation, see for example:

J. B. Buchanan, U.S. Pat. No. 3,576,834, Apr. 27, 1971, Col. 5, Line 36 through Col. 7, Line 70 and Ex. 1–4, 17, 106, 123–140.

R. R. Shaffer, U.S. Pat. No. 3,560,616, Feb. 2, 1971, Col. 3, Line 48, through Col. 7, Line 26 and Examples 3–9, 11–18.

E. Somers, "Formulation", Chapter 6 in Torgeson, "Fungicides", Vol. 1, Academic Press, New York, 1967.

EXAMPLE A

Wettable Powder 3-chloro-5-phenylthio-4H-1,2,6-thiadiazin-4-one: 40%
dioctyl sodium sulfosuccinate: 1.5%
sodium ligninsulfonate: 3%
low viscosity methyl cellulose: 1.5%
attapulgite: 54%

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE B

Wettable Powder 5-chloro-3-(4-chlorophenylthio)-4H-1,2,6-thiadiazin-4-one: 50%
sodium dioctylsulfosuccinate: 2%
low viscosity methyl cellulose: 1%
diatomaceous earth: 47%

The ingredients are blended, hammer-milled and then air milled to produce particles of active essentially all below 5 microns in diameter. The product is reblended before packaging.

EXAMPLE C

Wettable Powder 3-chloro-5-(4-chloro-3-methylphenoxy)-4H-1,2,6-thiadiazin-4-one: 80%
sodium alkylnaphthalenesulfonate: 2%
sodium ligninsulfonate: 2%
synthetic amorphous silica: 3%
kaolinite: 13%

The ingredients are hammer-milled to produce a wettable powder with greater than 95% of the particle below 44 microns in diameter.

EXAMPLE D

High Strength Concentrate 3-chloro-5-[4-(1,1-dimethylethyl)phenylthio]-4H-1,2,6-thiadiazin-4-one: 98.5%
silica aerogel: 0.5%
synthetic amorphous fine silica: 1.0%

The ingredients are blended and ground in an air mill to produce a high strength concentrate practically all below 20 microns diameter. This material may then be formulated in a variety of ways.

EXAMPLE E

Dust high strength concentrate, Example D: 25.4%
pyrophyllite, powdered: 74.6%

The ingredients are thoroughly blended and packaged for use.

EXAMPLE F

Emulsifiable Concentrate 5-chloro-3-(4-chlorophenylthio)-4H-1,2,6-thiadiazin-4-one: 10%
blend of oil soluble sulfonates and polyoxyethylene ethers: 5%
xylene: 85%

The ingredients are stirred to form a solution which may be emulsified in water for use.

EXAMPLE G

Solution 3-chloro-5-(2,4-dichlorophenoxy)-4H-1,2,6-thiadiazin-4-one: 20%
isophorone: 80%

The ingredients are combined and stirred to produce a solution suitable for direct, low volume application.

EXAMPLE H

Aqueous Suspension 3-chloro-5-(4-methylphenoxy)-4H-1,2,6-thiadiazin-4-one: 25%
hydrated attapulgite: 3%
crude calcium ligninsulfonate: 10%
sodium dihydrogen phosphate: 0.5%
water: 61.5%

The ingredients are ground together in a ball or roller mill until the solid particles have been reduced to diameters under 10 microns.

EXAMPLE I

Extruded Pellet 5-chloro-3-methylthio-4H-1,2,6-thiadiazin-4-one: 25%
anhydrous sodium sulfate: 10%
crude calcium ligninsulfonate: 5%
sodium alkylnaphthalenesulfonate: 1%
calcium/magnesium bentonite: 59%

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE J

Seed Treating Dust 3-chloro-5-(1-oxopyridin-2-ylthio)-4H-1,2,6-thiadiazin-4-one: 25%
Permanent Red 2-B Lake: 8%
Talc: 67%

The ingredients are blended and passed through a hammer mill to produce a powder suitable for dust treatment of seeds.

Use

The compounds of this invention are effective for the control of a broad spectrum of plant diseases incited by fungal pathogens represented by *Venturia inaequalis, Gymnosporangium juniperivirgininae, Uromyces phaseoli* var. *typica, Phytophthora infestans, Plasmopara viticola* and *Cercospora beticola*.

Disease control is accomplished by applying the compound to the portion of the plant or seed to be protected. Rates of application for these disease control agents will be influenced by many environmental factors and therefore optimum levels will be determined under use conditions. Generally rates of application of 0.1 to 2 kg/ha are suitable. In the greenhouse where a spray deposit is uniformly distributed and where disease is produced under controlled conditions, a spray concentration from 20 to 400 ppm can be effective for disease control.

Compositions of this invention may contain, in addition to one of the thiadiazinone compounds of this invention, conventional insecticides, nematicides, miticides, bactericides, fungicides or other agricultural chemicals such as growth modifying and fertilizer ingredients, and the like. The proper choice and amounts can be made by one skilled in the art of protecting plants from pest depredation.

In the following examples of disease control, the percent disease control was calculated by the formula $$100 - \left[ \frac{\text{disease rating on treated}}{\text{disease rating on untreated}} \times 100 \right] = \text{percent control}$$

EXAMPLE I

Compounds of this invention were dissolved in acetone in an amount equal to 10% of the final volume and then suspended at a concentration of 80 ppm in purified water containing 250 ppm of the surfactant TREM ®014 (polyhydric alcohol esters). This suspension was sprayed to the point of run-off on seedling apple plants growing in pots and trained to a single shoot. The following day the apple seedlings were inoculated with a spore suspension of the fungus *Venturia inaequalis* and incubated in a saturated humidity chamber at 20° C. for 24 hours, and then in a greenhouse for an additional eleven days when disease ratings were made.

The following table shows results for some of the compounds that are effective for controlling apple scab at 80 ppm:

| Compound | Percent Control Apple Scab |
|---|---|
| 3-chloro-5-(4-chlorophenylthio)-4H—1,2,6-thiadiazin-4-one | 96 |
| 3-chloro-5-[4-(1,1-dimethylethyl)phenylthio]-4H—1,2,6-thiadiazin-4-one | 96 |
| 3-chloro-5-(4-chlorophenylmethylthio)-4H—1,2,6-thiadiazin-4-one | 98 |
| 3-chloro-5-phenylthio-4H—1,2,6-thiadiazin-4-one | 99 |
| 3-chloro-5-(4-methylphenylthio)-4H—1,2,6-thiadiazin-4-one | 99 |
| 3-chloro-5-(3,4-dichlorophenylthio)-4H—1,2,6-thiadiazin-4-one | 83 |
| 3-chloro-5-(2,4-dichlorophenoxy)-4H—1,2,6-thiadiazin-4-one | 99 |
| 3-chloro-5-(2,3-dichlorophenoxy)-4H—1,2,6-thiadiazin-4-one | 99 |
| 3-chloro-5-(4-methylphenoxy)-4H—1,2,6-thiadiazin-4-one | 99 |
| 3-chloro-5-(4-chloro-3-methylphenoxy)-4H—1,2,6-thiadiazinone | 99 |

EXAMPLE II

Compounds of the invention were dissolved in acetone in an amount equal to 10% of the final volume, and then suspended at a concentration of 80 ppm in purified water containing 250 ppm of the surfactant TREM ®014 (polyhydric alcohol esters). This suspension was sprayed to the point of run-off on the apple trees. The next day the apples were inoculated with spores of the fungus, *Gymnosporangium juniperivirgininae*. The inoculated apple trees were incubated in a saturated humidity chamber at 20° C. for 24 hours, and then in a greenhouse for an additional 10 days when disease ratings were made.

The following table shows results for two of the compounds that are effective for control of cedarapple rust at 80 ppm:

| Compound | Percent Control Cedar-Apple Rust |
|---|---|
| 3-chloro-5-(4-chlorophenylthio)-4H—1,2,6-thiadiazin-4-one | 87 |
| 3-chloro-5-[4-(1,1-dimethylethyl)phenylthio]-4H—1,2,6-thiadiazin-4-one | 90 |

EXAMPLE III

Compounds of this invention were dissolved in acetone and then suspended at a concentration of 80 ppm in purified water containing 250 ppm of the surfactant TREM ®014 (polyhydric alcohol esters). This suspension was sprayed to the point of run-off on tomato plants growing in the greenhouse. The next day the plants were inoculated with a spore suspension of the fungus, *Phytophthora infestans*. The chemically-sprayed and inoculated tomato plants were incubated in a saturated humidity at 20° C. for 24 hours and then in a greenhouse an additional three days when disease ratings were made.

The following table shows results for some of the compounds that are effective for controlling late blight at 80 ppm:

| Compound | Percent Control Tomato Late Blight |
|---|---|
| 3-chloro-5-(4-chlorophenylthio)-4H—1,2,6-thiadiazin-4-one | 82 |
| 3-chloro-5-[4-(1,1-dimethylethyl)phenylthio]-4H—1,2,6-thiadiazin-4-one | 65 |
| 3-chloro-5-(4-methylphenylthio)-4H—1,2,6-thiadiazin-4-one | 91 |
| 3-chloro-5-(2,4-dichlorophenoxy)-4H—1,2,6-thiadiazin-4-one | 72 |
| 3-chloro-5-(4-methylphenoxy)-4H—1,2,6-thiadiazin-4-one | 97 |
| 3-chloro-5-(3-chloro-4-methylphenoxy)-4H—1,2,6-thiadiazin-4-one | 90 |

EXAMPLE IV

Compounds of this invention were dissolved in acetone in an amount equal to 10% of the final volume and then suspended at a concentration of 80 ppm in purified water containing 250 ppm of the surfactant TREM ®014 (polyhydric alcohol esters). This suspension was sprayed to the point of run-off on Pinto beans grown 10 days in pots in the greenhouse. The next day the plants were inoculated with a spore suspension of the fungus, *Uromyces phaseoli* var. *typica*. The inoculated bean plants were incubated in a saturated humidity chamber at 20° C. for 24 hours and then in a greenhouse for an additional week when disease ratings were made.

The following table shows results for some of the compounds that are effective for control of bean rust at 80 ppm:

| Compound | Percent Control Bean Rust |
|---|---|
| 3-chloro-5-(4-chlorophenylthio)-4H—1,2,6-thiadiazin-4-one | 96 |
| 3-chloro-5-[4-(1,1-dimethylethyl)phenylthio]-4H—1,2,6-thiadiazin-4-one | 94 |
| 3-chloro-5-(4-chlorophenoxy)-4H—1,2,6-thiadiazin-4-one | 98 |
| 3-chloro-5-(4-methoxyphenoxy)-4H—1,2,6-thiadiazin-4-one | 88 |
| 3-chloro-5-(4-chloro-3-methylphenoxy)-4H—1,2,6-thiadiazin-4-one | 98 |
| 3-chloro-5-(2,5-dichlorophenoxy)-4H—1,2,6-thiadiazin-4-one | 99 |

EXAMPLE V

Compounds of this invention were dissolved in acetone and then suspended at a concentration of 80 ppm in purified water containing 250 ppm of the surfactant TREM ®014 (polyhydric alcohol esters). The suspension was sprayed to the point of run-off on grape plants growing in pots in a greenhouse. The next day the plants were inoculated with a spore suspension of the fungus, *Plasmopara viticola* and incubated in a saturated humidity at 20° C. for 3 days, in the greenhouse 4 days, and back into the saturated humidity for 3 more days when disease ratings were made.

The following table shows results for some of the compounds that are effective for controlling grape downy mildew at 80 ppm:

| Compound | Percent Control Grape Downy Mildew |
|---|---|
| 3-chloro-5-(4-chlorophenylthio)-4H—1,2,6-thiadiazin-4-one | 99 |
| 3-chloro-5-[4-(1,1-dimethylethyl)phenylthio]-4H—1,2,6-thiadiazin-4-one | 99 |

EXAMPLE VI

Four week old sugar beets were sprayed uniformly to the point of run-off with a dispersion consisting of acetone, purified water, 500 ppm of the surfactant TREM ®014 (polyhydric alcohol esters) and the compounds of this invention at 100 ppm. After 24 hours, the sugar beets were inoculated with a spore suspension of *Cercospora beticola* and incubated in a saturated humidity chamber at 22° to 26° C. for 72 hours. After 21 days of incubation in the greenhouse, disease ratings were made.

The following table shows results for some of the compounds for the control of *Cercospora beticola*:

| Compound | Percent Control Cercospora beticola |
|---|---|
| 3-chloro-5-[4-(1,1-dimethylethyl)phenylthio]-4H—1,2,6-thiadiazin-4-one | 98 |
| 3-chloro-5-(4-chlorophenylthio)-4H—1,2,6-thiadiazin-4-one | 83 |

EXAMPLE VII

3-Chloro-5-[4-(1,1-dimethylethyl)phenylthio]-4H-1,2,6-thiadiazin-4-one was dissolved in an acetone base solvent and applied to corn seed as a seed coating treatment for the control of "damping off" disease caused by Pythium sp. Treated seeds were allowed to dry, planted in Pythium charged natural soils, held at 10° C. for 8 days, then allowed to germinate at a temperature of 20° C. Since corn seed attacked by Pythium fails to germinate, the percent germination serves as a good index for disease control.

Two separate tests with corn were conducted using 3-chloro-5-[4-(1,1-dimethylethyl)phenylthio]-4H-1,2,6-thiadiazin-4-one, a first test at a single rate (1.5 g ai/kg of seed) and a second test at 4 rates (2.5, 1.25, 0.63, 0.06 g ai/kg of seed). These tests were unreplicated and were planted in plastic cookie trays.

The following are the results of 3-chloro-5-[4-(1,1-dimethylethyl)phenylthio]-4H-1,2,6-thiadiazin-4-one on the two corn tests with crop phytotoxicity symptoms absent in all tests.

| | Rate, g ai/kg | % Pythium Control |
|---|---|---|
| | 1.5 | 100 |
| | 2.5 | 100 |
| | 1.25 | 100 |
| | 0.63 | 90 |
| | 0.06 | 90 |
| Untreated | — | 0 |

EXAMPLE VIII

The procedure of Example VII was employed except 3-chloro-5-methylthio-4H-1,2,6-thiadiazin-4-one was used instead of 3-chloro-5-[4-(1,1-dimethylethyl)-phenylthio]-4H-1,2,6-thiadiazin-4-one.

The following are results of 3-chloro-5-methylthio-4H-1,2,6-thiadiazin-4-one on the corn tests with crop phytotoxicity symptoms absent in all tests.

| Rate, g ai/kg | % Pythium Control |
|---|---|
| 1.5 | 70 |
| 2.5 | 90 |
| 1.25 | 90 |
| 0.63 | 90 |
| 0.06 | 0 |
| Untreated — | 0 |

"Consisting essentially of" is intended to have its customary meaning: namely, that all specified materials and conditions are very important in practicing the invention but that unspecified materials and conditions are not excluded so long as they do not prevent the benefits of the invention from being realized.

I claim:

1. An agricultural composition consisting essentially of a diluent, surfactant or mixtures thereof and a fungicidally effective amount of a compound of the formula

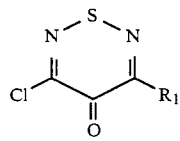

wherein
$R_1 = SR_2$,
$R_2 =$ alkyl of 1 to 6 carbon atoms,

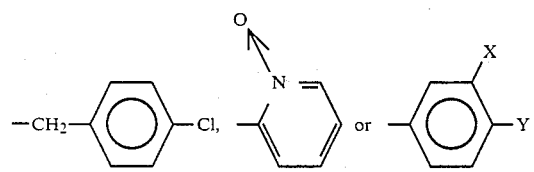

$X = H$ or $Cl$
$Y = H$, $Cl$ or alkyl of 1 to 4 carbon atoms
provided that when $X = Cl$, then $Y = Cl$.

2. The composition of claim 1 where $R_2 = CH_3$,

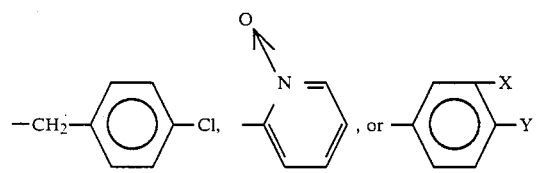

where $X = H$.

3. The composition of claim 2 where $R_2 = CH_3$,

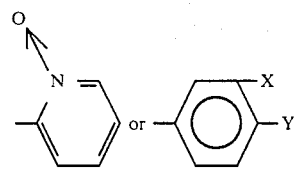

where $X = H$ and $Y = H$, $Cl$ or $C(CH_3)_3$.

4. The composition of claim 3 where $R_2 =$ methyl.

5. The composition of claim 3 where $R_2 =$

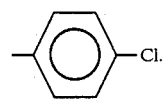

6. The composition of claim 3 where $R_2 =$

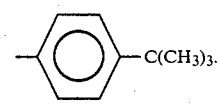

7. A method for controlling a fungus disease of a plant or seed which comprises applying to the plant or seed a fungicidally effective amount of a compound of the formula

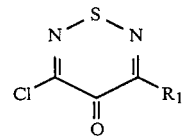

wherein
$R_1 = SR_2$,
$R_2 =$ alkyl of 1 to 6 carbon atoms,

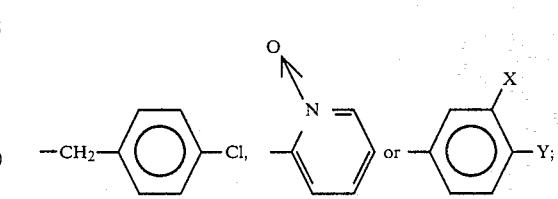

$X = H$ or $Cl$;
$Y = H$, $Cl$ or alkyl of 1 to 4 carbon atoms;
provided that when $X = Cl$, then $Y = Cl$.

8. The method of claim 7 where $R_2 = CH_3$,

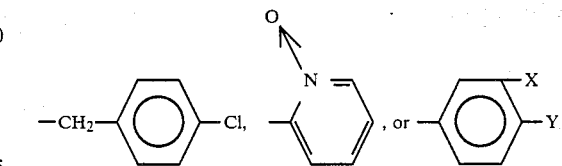

where $X = H$.

9. The method of claim 8 where $R_2 = CH_3$,

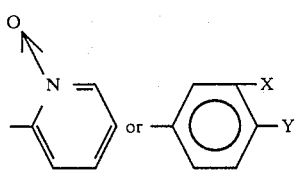
where X=H and Y=H, Cl or C(CH₃)₃.
10. The method of claim 9 where $R_2$=methyl.
11. The method of claim 9 where $R_2$=
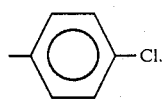
12. The method of claim 9 where $R_2$=
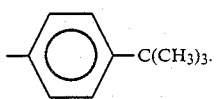
* * * * *